(12) United States Patent
Bylsma

(10) Patent No.: US 6,221,078 B1
(45) Date of Patent: Apr. 24, 2001

(54) SURGICAL IMPLANTATION APPARATUS

(76) Inventor: Stephen S. Bylsma, 175 Pioneer Cir., Arroyo Grande, CA (US) 93420

( * ) Notice: Subject to any disclaimer, the term of this patent is extended or adjusted under 35 U.S.C. 154(b) by 0 days.

(21) Appl. No.: 09/344,355

(22) Filed: Jun. 25, 1999

(51) Int. Cl.$^7$ .................................................. A61F 9/00
(52) U.S. Cl. ............................................................ 606/107
(58) Field of Search .................................... 606/107, 108, 606/166, 170, 172, 182; 604/57, 59, 60, 64, 164.01, 164.06, 164.09

(56) References Cited

U.S. PATENT DOCUMENTS

| | | | |
|---|---|---|---|
| 4,665,918 | * | 5/1987 | Garza et al. .......................... 606/108 |
| 5,098,439 | * | 3/1992 | Hill et al. ............................. 606/107 |
| 5,183,463 | * | 2/1993 | Debbas ................................. 604/98 |
| 5,484,444 | * | 1/1996 | Braunschweiler et al. ........... 606/108 |
| 5,494,484 | * | 2/1996 | Feingold .............................. 606/107 |
| 5,501,664 | * | 3/1996 | Kaldany ................................ 604/57 |
| 5,571,168 | * | 11/1996 | Toro .................................... 606/108 |
| 5,895,401 | * | 4/1999 | Daum et al. ......................... 606/170 |

* cited by examiner

*Primary Examiner*—Jeffrey A. Smith
*Assistant Examiner*—Eduardo C. Robert
(74) *Attorney, Agent, or Firm*—William L. Klima; Law Offices of William L. Klima, PLC

(57) ABSTRACT

An apparatus for introducing a glaucoma drain to the eye includes an outer hub including a longitudinal slot, a nosepiece retractably mounted within said outer hub, a handle having a gripping portion and an extending portion, the extending portion removably attached to the retractable nosepiece through the longitudinal slot in the outer hub, and a tool operably disposed within the retractable nosepiece within the outer hub. Tools provided with the apparatus include a stylette configured to prepare an eye for introduction of a glaucoma drain thereto and a plunger configured for introducing a glaucoma drain from the retractable nosepiece to the eye.

17 Claims, 4 Drawing Sheets

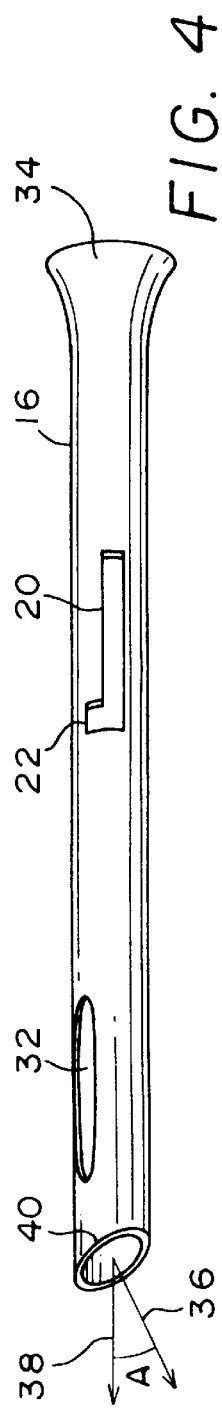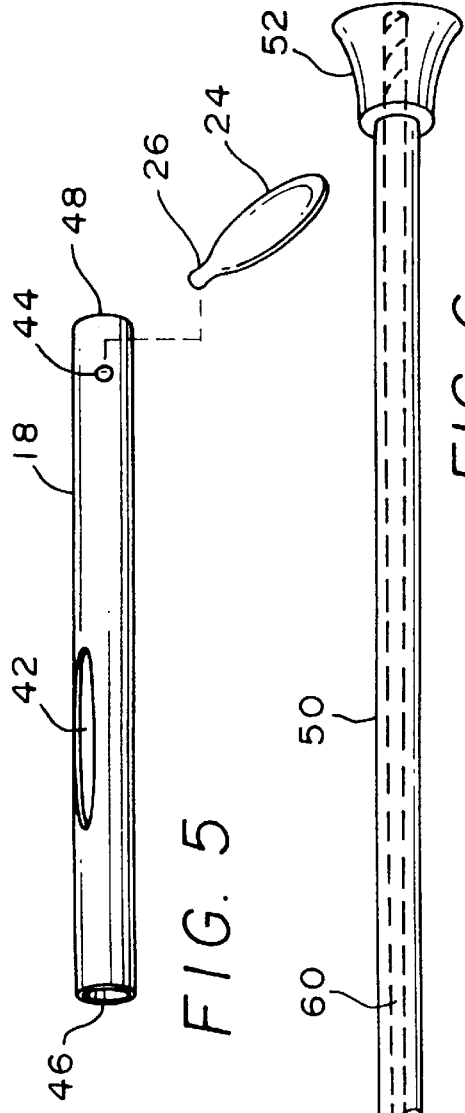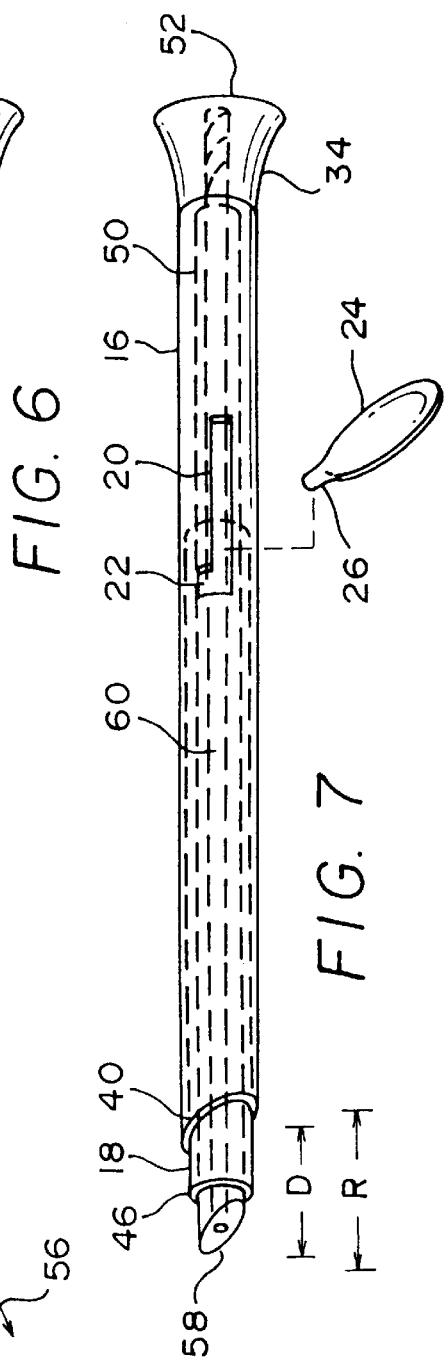

SURGICAL IMPLANTATION APPARATUS

FIELD OF THE INVENTION

The present invention is directed to surgical devices and more specifically to an apparatus for introducing a glaucoma drain to the eye of a human or animal.

BACKGROUND OF THE INVENTION

Aqueous humor, the fluid of the eye, is produced by the ciliary body in the posterior chamber. In the normal eye, the fluid migrates into the anterior chamber and filters through the trabecular meshwork into the canal of Schlemm. The canal of Schlemm drains into veins which carry the aqueous humor away from the eye.

Intraocular pressure is a function of the rate at which aqueous humor is produced in and released from the eye. Glaucoma is a disease of the eye characterized by an abnormally high intraocular pressure. Usually, glaucoma is caused by a problem with release, as opposed to production, of aqueous humor.

One method of treating glaucoma is to surgically introduce a drainage device to the eye. Such devices are generally configured to provide a controlled release of aqueous humor to alleviate intraocular pressure. It is critical to the proper functioning of these devices that they be introduced to the eye properly.

SUMMARY OF THE INVENTION

Accordingly, it is a first object of the present invention to provide an apparatus for introducing a glaucoma drain to the eye.

It is a second object of the present invention to provide an improved apparatus for introducing a glaucoma drain to the eye.

It is a third object of the present invention to provide an apparatus which is configured such that the distal end thereof closely contours the surface of the eye.

It is a fourth object of the present invention to provide an apparatus device which is easy to use.

It is a fifth object of the present invention to provide an apparatus which is configured such that an operable portion thereof is encased until placed into position proximal to the eye.

It is a sixth object of the present invention to provide an apparatus device which is safe to use.

It is a seventh object of the present invention to provide an apparatus device which may be used to perform multiple functions involved in the introduction of a glaucoma drain to the eye.

It is an eighth object of the present invention to provide an apparatus for introducing a glaucoma drain to the eye including an outer hub including a longitudinal slot, a nosepiece retractably mounted within the outer hub, a handle having a gripping portion and an extending portion, the extending portion removably attached to the retractable nosepiece through the longitudinal slot in the outer hub, and, a tool operably disposed within the retractable nosepiece within the outer hub.

It is a ninth object of the present invention to provide a method of introducing a glaucoma drain to the eye including the steps of inserting a stylette into a retractable nosepiece slidably mounted within an outer hub, retracting the nosepiece into the outer hub, operating said stylette to create a small wound in the eye at a location along the periphery of the cornea, removing the stylette from the retractable nosepiece and the outer hub, extending the retractable nosepiece, loading a glaucoma drain into a distal end of the retractable nosepiece, inserting a plunger having a plunger tip including a planar end face into the retractable nosepiece slidably disposed within the outer hub, retracting the nosepiece into the outer hub, placing the outer hub in contact with the eye over the wound, and, operating the plunger to advance the glaucoma drain out the distal end of the retractable nosepiece and into the wound.

The present invention provides an apparatus for introducing a glaucoma drain to the eye. A preferred embodiment of the apparatus includes a tubular elongated outer hub having an open flared proximal end. The outer hub also has an open distal end which defines a plane having a normal which intersects the longitudinal axis of the outer hub at an angle.

A preferred embodiment of the apparatus also includes a tubular retractable nosepiece disposed within the outer hub. A longitudinal slot in the outer hub is configured such that the extending portion of a handle may pass therethrough and threadedly engage the retractable nosepiece. The slot provides a range of motion for the retractable nosepiece relative to the outer hub. Specifically, the extending portion of the handle on the nosepiece travels within the slot to allow the nosepiece to extend and to retract relative to the outer hub. The slot in the outer hub also includes a transverse portion, preferably, located at the distal end of the slot, for locking the nosepiece relative to the outer hub, preferably, in an extended position.

The outer hub and retractable nosepiece are adapted to receive a glaucoma drain tool. Specifically, the apparatus is provided with a stylette having a flared proximal end which is configured to engage the flared proximal end of the outer hub when the stylette is inserted therein. The distal end of the stylette defines a plane having a normal which intersects the longitudinal axis of the stylette at an angle. The stylette is preferably configured such that when the retractable nosepiece is an extended position, the distal end of the stylette does not extend beyond the distal end of the retractable nosepiece.

The apparatus is also preferably provided with an elongated cylindrical plunger having a planar end faced plunger tip. The plunger tip is configured for translating a glaucoma drain out of the retractable nosepiece and into the tissue of the eye. The plunger further includes a collar which is configured to engage the outer hub to prevent the plunger tip from extending beyond the retractable nosepiece when the retractable nosepiece is an extended position. The plunger also includes a thumb rest at the proximal end thereof.

In a preferred method of introducing a glaucoma drain to the eye with the present invention, the apparatus is brought into position proximally to the eye with the stylette operably disposed within the retractable nosepiece and outer hub. The retractable nosepiece is preferably in an extended position with the extending portion of the handle locked into the transverse portion of the slot in the outer hub.

Once in position near the eye, the retractable nosepiece is retracted into the outer hub by disengaging the extending portion of the handle from the transverse portion of the slot in the outer hub and sliding the nosepiece proximally relative to the outer hub. The open distal end of the outer hub is angled, as described above, relative to the longitudinal axis of the outer hub. This feature allows the longitudinal axis of the apparatus to be perpendicular to the face of the patient and simultaneously for the distal end of the outer hub to closely contour the curved surface of the eye thus providing an improved surgical orientation of the apparatus for the surgeon.

With the outer hub in contact with the eye at a location along the periphery of the cornea, the stylette is then advanced to create a small wound in the eye. The diameter of the wound is controlled by the diameter of the stylette. The stylette is preferably provided with a through bore such that a small volume of tissue is excised during formation of the wound. The depth of the ocular wound is limited by the extent to which the distal end of the stylette extends beyond the distal end of the outer hub when the flared proximal end of the stylette engages the flared proximal end of the outer hub. Wound depth may therefore by easily configured according to the dimensions of the glaucoma drain to be introduced to the eye with the apparatus.

Once the ocular wound is formed in the eye, the apparatus is moved away from the eye and the stylette is removed from the outer hub and retractable nosepiece. The retractable nosepiece is returned to and locked in the extended position. A glaucoma drain, preferably, a small cylindrical section of porous biocompatible material, is loaded into the distal end of the retractable nosepiece. The plunger is then inserted into the proximal end of the outer hub and the apparatus is again brought into close proximity to the eye and specifically to the ocular wound created with the apparatus. Again, the retractable nosepiece is placed in a retracted position. The plunger is then moved distally such that the plunger tip engages the glaucoma drain. With the distal end of the outer hub in contact with the surface of the eye, the plunger is further advanced causing the plunger tip to translate the glaucoma drain out the distal end of the retractable nosepiece and into the ocular wound, thereby introducing the glaucoma drain to the eye.

BRIEF DESCRIPTION OF THE DRAWINGS

FIG. 4 shows a side view of a preferred embodiment of an outer hub according to the present invention.

FIG. 5 shows an exploded side view of a retractable nosepiece and handle assembly according to the present invention.

FIG. 6 shows a side view of a stylette according to the present invention.

FIG. 7 shows a side view of an assembly including an outer hub, retractable nosepiece, handle, and stylette according to the present invention.

DETAILED DESCRIPTION OF THE PREFERRED EMBODIMENT

Figure 1:
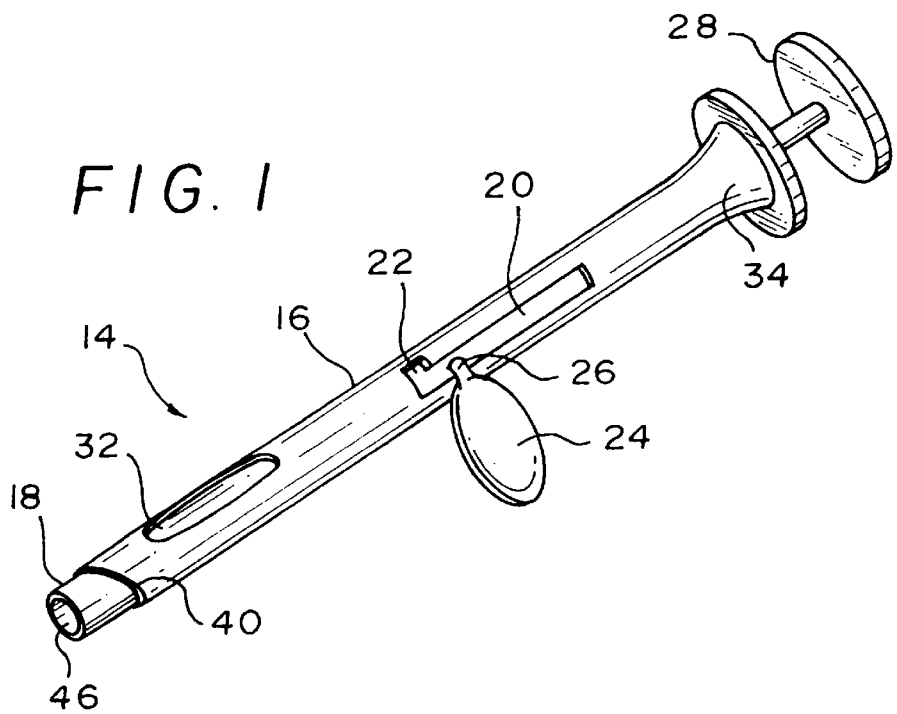
FIG. 1 shows a perspective view of a preferred embodiment of an apparatus for introducing a glaucoma drain to the eye according to the present invention.

FIG. 1 shows a perspective view of a preferred embodiment of an apparatus 14 for introducing a glaucoma drain to the eye according to the present invention. Apparatus 14 includes an elongated tubular outer hub 16 including a longitudinal slot 20 having a transverse portion 22 as shown in FIGS. 1–4. Outer hub 16 also includes a flared proximal end 34 and a distal gripping portion 32. As shown in FIG. 4, the distal end 40 of outer hub 16 defines a plane having a normal 36 which forms an angle, A, with the longitudinal axis 38 of outer hub 16. Outer hub 16 preferably has a length of about 15 mm and a diameter of about 1 mm. Flared proximal end 34 is preferably about 2 mm in diameter and angle, A, is preferably about 45 degrees.

Figure 2:
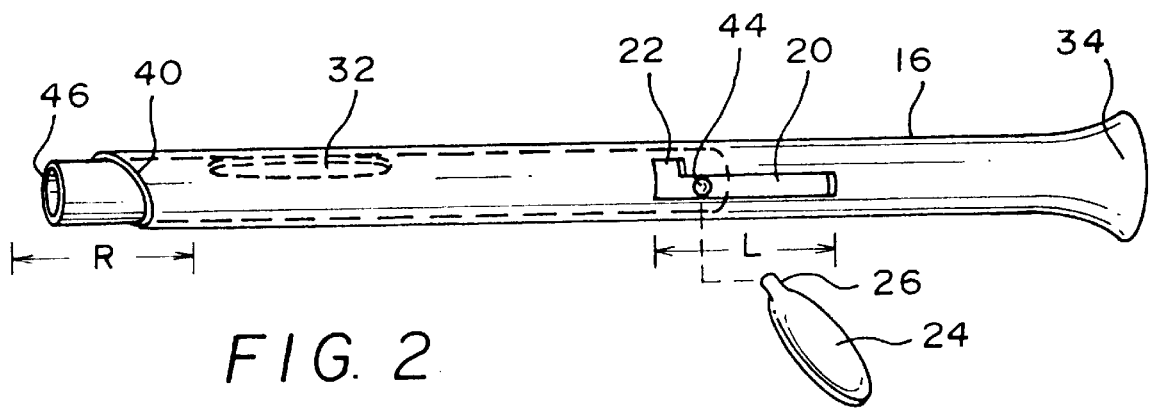
FIG. 2 shows a partial exploded side view of an outer hub, a retractable nosepiece and a handle assembled according to the present invention with the retractable nosepiece in a partially extended position.
Figure 3:
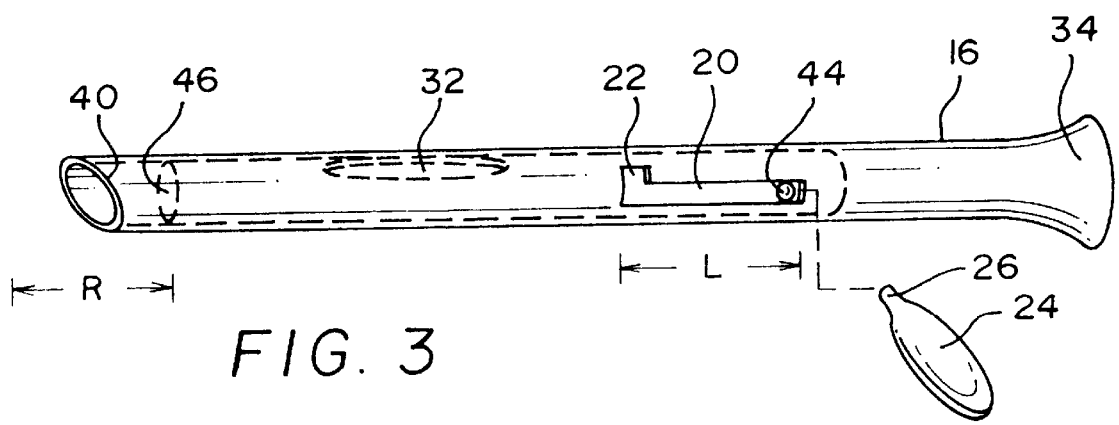
FIG. 3 shows the assembly shown in FIG. 2 with the retractable nosepiece in a fully retracted position.

Apparatus 14 further includes a nosepiece 18 which is configured to retract into outer hub 16. As shown in FIG. 5, nosepiece 18 is a relatively short tubular portion having a distal gripping portion 42 and a threaded proximal hole 44. As is further shown in FIG. 5, a handle 24 including an extending portion 26 having a threaded end is configured to engage threaded proximal hole 44 in nosepiece 18. Nosepiece 18 preferably has a length of about 10 mm and a diameter of about 1 mm. The length of handle 24 including extending portion 26 is preferably about 5 mm. nosepiece 18 is disposed within outer hub 16 such that threaded hole 44 aligns with slot 20, as shown in FIGS. 1–3. The threaded end of extending portion 26 of handle 24 is then passed through slot 20 and attached to nosepiece 18, thereby slidably mounting nosepiece 18 to outer hub 16. Note that relative axial movement between nosepiece 18 and outer hub 16 is limited by length, L, of slot 20 as shown in FIG. 2 and 3. Further note that length, L, is configured such that the range, R, of the distal end 46 of nosepiece 18 beyond or behind the distal end 40 of outer hub 16, is precisely limited.

The transverse portion 22 of slot 20 in outer hub 16 is configured to receive extending portion 26 of handle 24, and thereby lock nosepiece 16 in a fully extended axial position relative to outer hub 18. When nosepiece 16 is in a locked position (not shown), the distance by which distal end 46 of nosepiece 18 extends beyond the distal end 40 of outer hub 16 is at a maximum.

FIG. 2 shows nosepiece 18 in a partially extended position relative to outer hub 16. Distal end 46 of nosepiece 18 extends beyond distal end 40 of outer hub 16. In FIG. 3 nosepiece 18 is shown in a fully retracted position. Distal end 46 of nosepiece 18 is shown within outer hub 16 when nosepiece 18 is in a retracted position.

The assembly shown in FIGS. 2 and 3 is configured such that a tool may be operably disposed therein. FIG. 6 shows a stylette 50 which is configured for use in the assembly of FIGS. 2 and 3. Specifically, as shown in FIGS. 6 and 7, stylette 50 includes a flared proximal end 52 which is configured to engage the flared proximal end 34 of outer it hub 16. Further, the distal end 58 of stylette defines a plane the normal 56 of which intersects the longitudinal axis of stylette 50 at an angle B. Preferably, angle B of stylette 50 is equal to angle A of outer hub 16, in FIG. 4. As will be further described later, stylette 50 also includes a through bore 60. Stylette 50 preferably has an overall length of about 17 mm. The diameter of stylette 50 at the distal end thereof is preferably about 0.6 mm and at the flared proximal end, about 2 mm.

FIG. 7 shows stylette 50 fully engaged with, in other words, fully inserted into outer hub 16. Further, nosepiece 18 is shown in a partially extended position relative to outer hub 16. Note that the distal end 58 of stylette 50 extends beyond the distal end 40 of outer hub 16 by a distance, D. It is important to recognize that if nosepiece 18 were in a fully extended position, the distal end 46 of nosepiece 18 would extend at least as far as the distal end 58 of stylette 50. In other words, the portion of range, R, shown in FIG. 2, outside of outer hub 16 is at least as great as distance, D.

Figure 8:
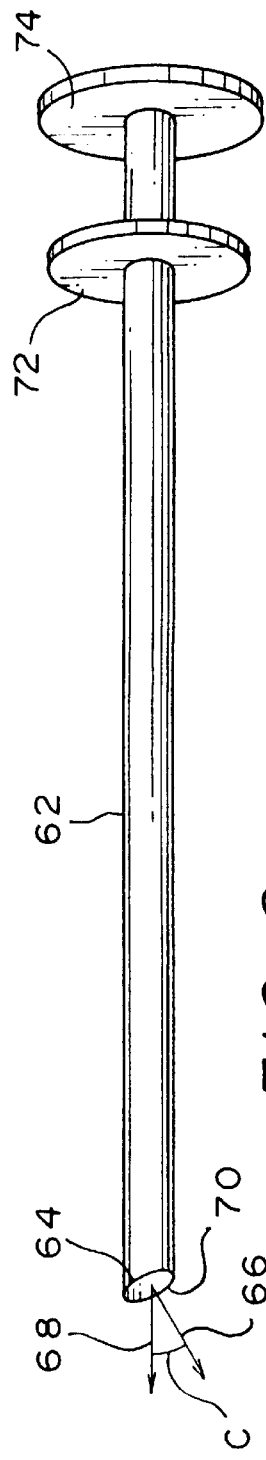
FIG. 8 shows a side view of a plunger according to the present invention.
Figure 9:
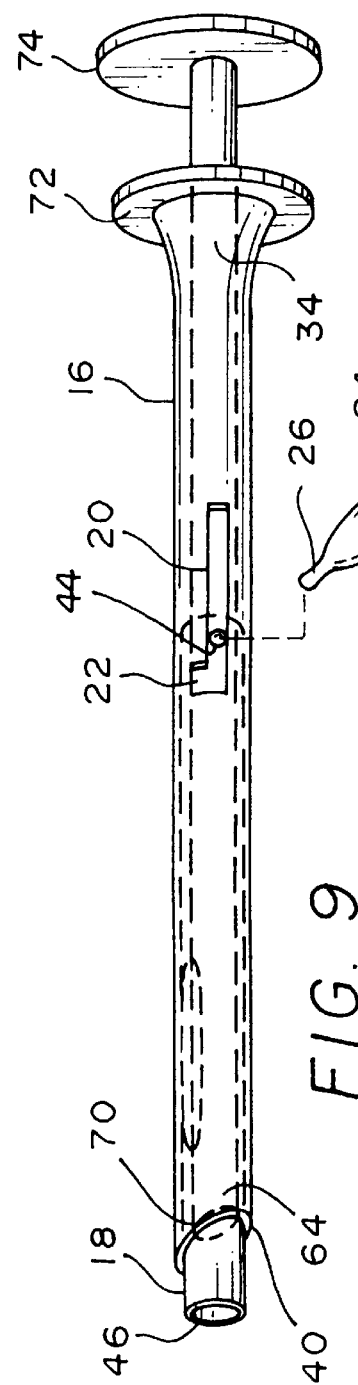
FIG. 9 shows a side view of an assembly including an outer hub, retractable nosepiece, handle and plunger with the nose piece in a partially extended position according to the present invention.
Figure 10:
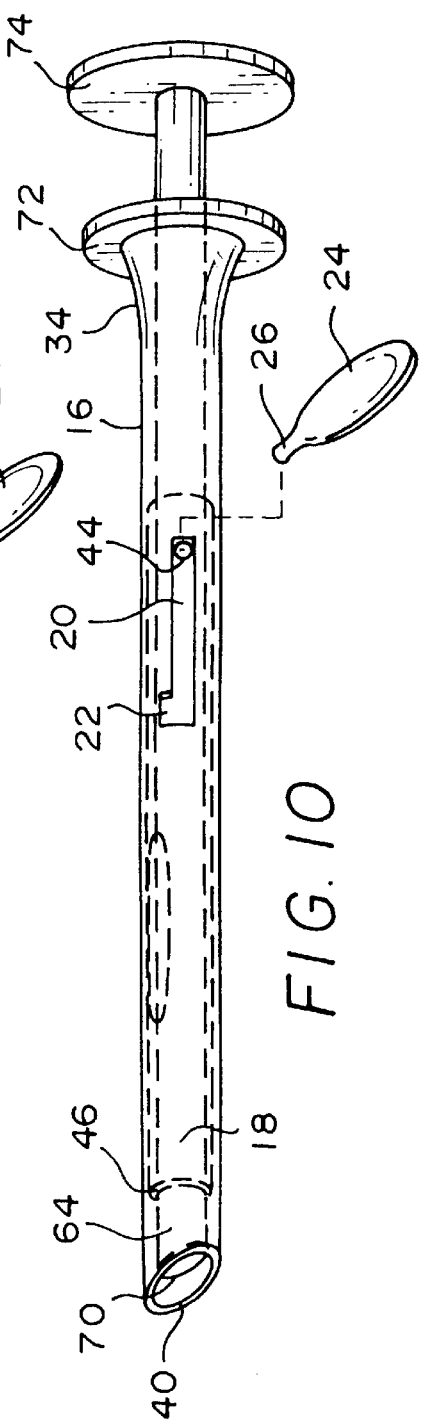
FIG. 10 shows a side view of the assembly shown in FIG. 9 with the retractable nosepiece in a fully retracted position.

FIG. 8 shows an elongated cylindrical plunger 62 which is configured for use in the assembly of FIGS. 2 and 3. Plunger 62 includes a plunger tip portion 64 having an end face 70 which defines a plane having a normal 66 which intersects the longitudinal axis 68 of the plunger at an angle, C, as shown in FIG. 8. Preferably, angle C is equal to angle A and angle B. Plunger 62 also includes a collar 72, which as shown in FIGS. 9 and 10, limits the distal axial movement of plunger 62 relative to outer hub 16 when plunger 62 is inserted therein as shown in FIGS. 9 and 10. Plunger 62 also includes a thumb rest 74 attached to the proximal end thereof Plunger 62 preferably has an overall length of about 15 mm and a diameter of about 0.70 mm.

As shown in FIGS. 9 and 10, the end face 70 of plunger tip portion 64 remains within outer hub 18 when plunger 62 is fully inserted within nosepiece 18 and outer hub 16, in other words, when collar 72 is in contact with the flared distal end 34 of outer hub 16. FIG. 9 shows nosepiece 18 in a partially extended position relative to outer hub 16 and FIG. 10 shows nosepiece 18 in a fully retracted position within outer hub 16.

In a preferred method of using apparatus 14 for introducing a glaucoma drain to the eye according to the present invention, stylette 50 is inserted into outer hub 16 and nosepiece 18 as shown in FIG. 7. Nosepiece 18 is preferably in an extended position and extending portion 26 of handle 24 is preferably locked into the transverse portion 22 of longitudinal slot 20. The apparatus is then brought into close proximity to the eye.

Figure 11:
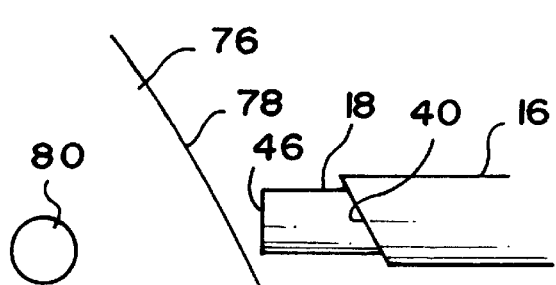
FIG. 11 shows a distal portion of an apparatus according to the present invention in close proximity to the surface of an eye.

As FIG. 11 shows the distal portion of apparatus 14 is preferably brought into close proximity to the surface 78 of the eye 76 near the canal of Schlemm 80. Note that distal end 46 of nosepiece 18 extends beyond the distal end 40 of outer hub 16 when nosepiece 18 is in an extended position.

Figure 12:
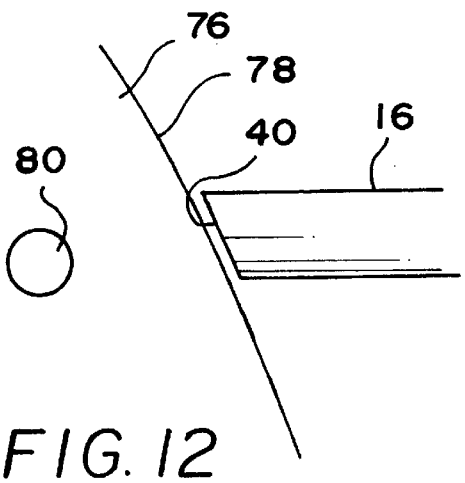
FIG. 12 shows a distal portion of an apparatus according to the present invention with the nosepiece retracted in close proximity to the surface of an eye.
Figure 13:
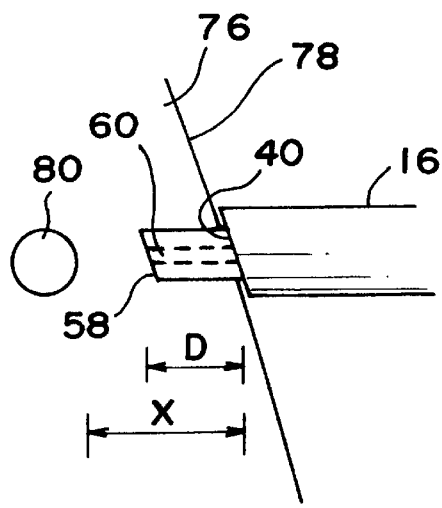
FIG. 13 shows a distal portion of an apparatus according to the present invention with a stylette penetrating the eye.

Nosepiece 18 is then retracted into outer hub 16 as shown in FIG. 12 and the distal end 40 of outer hub is brought into contact with the surface 78 of eye 76. Note that the distal end 40 of outer hub 16 closely contours the surface 78 of eye 76. Stylette 50 is then operated to create a wound in the eye 78 as shown in FIG. 13. The through bore 60 in stylette 50 is preferably configured such that a small portion of tissue is captured therein during creation of the wound in the eye. As shown in FIGS. 7 and 13, stylette 50 is advanced into outer hub 16 until the flared proximal end 52 thereof engages the flared proximal end 34 of outer hub 16.

As discussed above and shown in FIGS. 7 and 13, stylette 50 is configured such that the distal end 58 thereof extends a predetermined distance, D, beyond the distal end 40 of outer hub 16. Accordingly the wound created by apparatus 14 has a depth, D. Distance, D, is preferably configured to approach the depth, X, of the canal of Schlemm under the surface of the eye as shown in FIG. 13.

Figure 14:
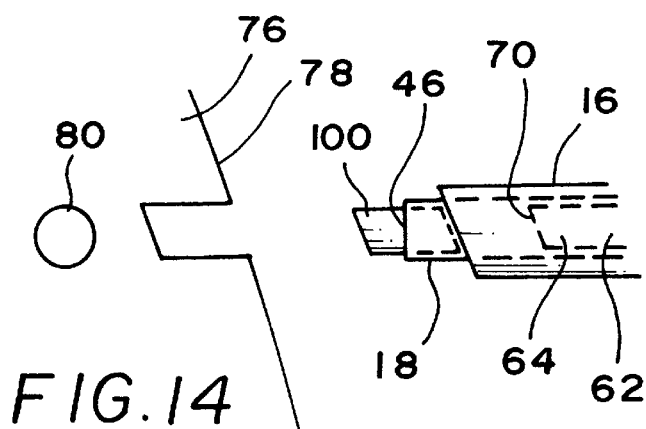
FIG. 14 shows a distal portion an apparatus according to the present invention with a glaucoma drain loaded into the nosepiece thereof

After creation of the wound, stylette 50 is withdrawn from the eye 78 and the apparatus. Nosepiece 18 is then placed into a fully extended position and a glaucoma drain 100 made of a cylindrical section of porous biomaterial is loaded into the distal end 46 thereof as shown in FIG. 14. Note that glaucoma drain 100 is configured dimensionally according to the wound in eye 76. Once glaucoma drain 100 is loaded into the distal end of nosepiece 18, plunger 62 is only partially inserted into outer hub 16 and nosepiece 18 as is further shown in FIG. 14.

Figure 15:
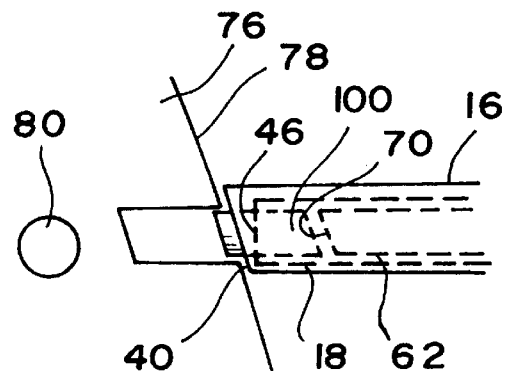
FIG. 15 shows a distal portion of an apparatus according to the present invention with a glaucoma drain partially introduced to the eye.
Figure 16:
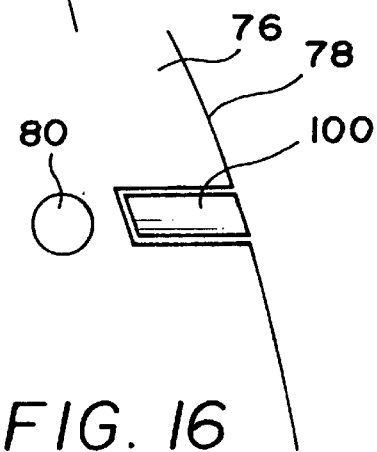
FIG. 16 shows a glaucoma drain introduced to an eye with an apparatus according to the present invention.

Nosepiece 18 is then fully retracted into outer hub 16 as shown in FIG. 15. Note that when nosepiece 18 is in a fully retracted position, a portion of glaucoma drain 100 remains extended beyond the distal end 40 of outer hub 16. The apparatus is then brought into close proximity to the eye 78 such that glaucoma drain 100 engages the wound in eye 76 and the distal end 40 of outer hub 16 contacts the surface 78 thereof. Plunger 62 is then advanced such that the distal end 70 thereof contacts the proximal surface of the glaucoma drain 100. Note that the plunger tip end face 70 is configured to engage the proximal surface of the glaucoma drain 100. Plunger 62 is advanced until collar 72 engages the proximal end 34 of outer hub 16 as shown in FIGS. 9 and 10. Glaucoma drain 100 is thereby translated out of the distal end of nosepiece 18 and outer hub 16 and into the wound in the eye 76 as shown in FIG. 16. The apparatus is then removed from close proximity to the eye thereby completing the introduction of a glaucoma drain to the eye with an apparatus according to the present invention.

What is claimed is:

1. An apparatus for introducing a glaucoma drain to the eye, comprising:

an elongated outer hub having a proximal end and a distal end, said outer hub includes a longitudinal slot;

a nosepiece retractable disposed within said outer hub, said nosepiece and said outer hub are configured such that relative axial movement therebetween is limited, said nosepiece includes a threaded hole;

a handle attached to said nosepiece, said handle includes an extending portion for sliding in said longitudinal slot in said outer hub and a threaded end for engaging said threaded hole of said nosepiece;

said nosepiece and said outer hub are configured such that relative axial movement therebetween may be selectively fixed;

a tool operably disposed within said retractable nosepiece and said outer hub, wherein said longitudinal slot in said outer hub includes a transverse portion into which said extending portion of said handle may be received for fixing said nosepiece axially relative to said outer hub and a distal end of said outer hub defines a plane having a normal which intersects with a longitudinal axis of said outer hub at a first angle.

2. An apparatus according to claim 1, wherein said tool is a stylette having a distal end configured to create a wound in an eye for introduction of a glaucoma drain thereto.

3. An apparatus according to claim 2, wherein said stylette is configured such that movement thereof relative to said outer hub is limited in a distal direction.

4. An apparatus according to claim 3, wherein said stylette is configured such that when said nosepiece is in a fully extended position relative to said outer hub and said stylette is in a fully extended position relative to said outer hub, said distal end of said nosepiece extends beyond said distal end of said stylette.

5. An apparatus according to claim 4, wherein said stylette includes a flared proximal end for engaging a flared proximal end of said outer hub.

6. An apparatus according to claim 5, wherein a distal end of said stylette defines a plane having a normal which intersects with said longitudinal axis of said stylette at a second angle.

7. An apparatus according to claim 6, wherein said stylette is provided with a longitudinal throughbore configured to excise a portion of tissue when said stylette is used to create a wound in an eye for introduction of a glaucoma drain thereto.

8. An apparatus according to claim 1, wherein said tool is a plunger configured for introducing a glaucoma drain from said retractable nosepiece to said eye.

9. An apparatus according to claim 8, wherein said plunger is configured such that movement thereof relative to said outer hub is limited in a distal direction.

10. An apparatus according to claim 9, wherein said plunger is configured such that when said plunger is in a fully extended position relative to said outer hub, at least a portion of said plunger tip portion of said plunger is within said outer hub.

11. An apparatus according to claim 10, wherein said plunger is provided with a thumb rest at a proximal end thereof and a collar portion for engaging a proximal end of said outer hub.

12. An apparatus according to claim 11, wherein said plunger tip portion is provided with an end face which defines a plane having a normal which intersects with said longitudinal axis of said plunger at a third angle.

13. An apparatus according to claim 12, wherein said first angle, said second angle, and said third angle, are equal.

14. An apparatus according to claim 13, wherein said first angle, said second angle, and said third angle, are equal to an angle defined by the angle between a plane tangential to a peak of a cornea and a plane tangential to a point on the periphery of said cornea.

15. A method of introducing a glaucoma drain to the eye including the steps of, inserting a stylette into a retractable nosepiece slidably disposed within an outer hub;

retracting said nosepiece into said outer hub;

operating said stylette to create a wound in an eye along the periphery of the cornea;

removing said stylette from said retractable nosepiece and said outer hub;

extending said retractable nosepiece;

loading a glaucoma drain into a distal end of said retractable nosepiece;

inserting a plunger having a plunger tip into said retractable nosepiece slidably disposed within said outer hub;

retracting said nosepiece into said outer hub;

placing said outer hub in contact with said eye over said wound; and, operating said plunger to translate said glaucoma drain out said distal end of said retractable nosepiece and into said wound.

16. A method according to claim 15, wherein said operating of said stylette step is further defined by displacing tissue of the eye to create a wound.

17. A method according to claim 16, wherein said operating of said stylette step is further defined by removing tissue of the eye to create a wound.

* * * * *